(12) United States Patent
Gottenbos et al.

(10) Patent No.: US 10,028,811 B2
(45) Date of Patent: Jul. 24, 2018

(54) DROPLET JET SYSTEM FOR CLEANSING

(75) Inventors: Bart Gottenbos, Budel (NL); Jozef Johannes Maria Janssen, Herten (NL); Marinus Karel Johannes Jager, Sammamish, WA (US); Adriaan Willem Cense, Eindhoven (NL); Paulus Corenlis Duineveld, Drachten (NL); Jon W. Hayenga, Redmond, VA (US); William E. Bryant, North Bend, WA (US); Martijn Jeroen Dekker, Groningen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1506 days.

(21) Appl. No.: 11/814,060

(22) PCT Filed: Jan. 20, 2005

(86) PCT No.: PCT/IB2005/050244
§ 371 (c)(1),
(2), (4) Date: Aug. 6, 2008

(87) PCT Pub. No.: WO2005/070324
PCT Pub. Date: Aug. 4, 2005

(65) Prior Publication Data
US 2009/0017423 A1    Jan. 15, 2009

Related U.S. Application Data
(60) Provisional application No. 60/537,690, filed on Jan. 20, 2004.

(51) Int. Cl.
*A61C 17/00*    (2006.01)
*A61C 17/02*    (2006.01)
*A61C 17/028*    (2006.01)

(52) U.S. Cl.
CPC ........ *A61C 17/0202* (2013.01); *A61C 17/028* (2013.01)

(58) Field of Classification Search
CPC .................... A61C 17/0202; A61C 17/028
(Continued)

(56) References Cited

U.S. PATENT DOCUMENTS 3,547,110 A * 12/1970 Balamuth .............. A61C 17/20
                                                      15/22.1
3,756,225 A *  9/1973 Moret .................... A61H 13/00
                                                      601/163
(Continued)

FOREIGN PATENT DOCUMENTS

CH         508396       6/1971
CH         508396 A     6/1971
(Continued)

OTHER PUBLICATIONS

Mark Anderson, "Design of Experiments", Sep. 1997, American Institute of Physics, pp. 24-26.*

*Primary Examiner* — Cris L Rodriguez
*Assistant Examiner* — Mirayda A Aponte

(57) ABSTRACT

The system includes a reservoir for fluid; a droplet generator for creating a stream of fluid droplets from the fluid wherein the velocity of the stream of droplets is within a range of 20 meters per second to 200 meters per second and the size of the droplets is within a range of 5 microns to 200 microns. A nozzle or nozzles direct the stream of droplets to safely clean a selected tooth or teeth surface area. The specific momentum of effective fluid droplets within the stream of fluid droplets is important in safe and effective cleaning.

3 Claims, 3 Drawing Sheets

(58) Field of Classification Search
USPC ......... 433/80, 81; 601/162, 163; 128/66, 62,
128/224, 320; 239/8, 738, 747, 204, 206,
239/237, 369, 381
See application file for complete search history.

(56) References Cited

U.S. PATENT DOCUMENTS

| | | | |
|---|---|---|---|
| 3,870,039 A | | 3/1975 | Moret et al. |
| 4,012,842 A | * | 3/1977 | Vit ................................ 433/216 |
| 4,906,187 A | * | 3/1990 | Amadera ............... A61C 17/02 |
| | | | 433/80 |
| 4,941,459 A | * | 7/1990 | Mathur ............. A61C 17/0214 |
| | | | 433/88 |
| 5,820,373 A | * | 10/1998 | Okano et al. .................... 433/80 |
| 6,030,215 A | * | 2/2000 | Ellion .................. A46B 11/001 |
| | | | 222/324 |
| 6,203,320 B1 | * | 3/2001 | Williams ............. A46B 11/063 |
| | | | 132/308 |
| 6,332,470 B1 | | 12/2001 | Fishkin et al. |
| 2003/0013063 A1 | * | 1/2003 | Goldman ............. A61C 1/0084 |
| | | | 433/80 |
| 2006/0097084 A1 | * | 5/2006 | Gromer et al. ................ 239/589 |

FOREIGN PATENT DOCUMENTS

| | | | | |
|---|---|---|---|---|
| DE | 8620898 | | 2/1987 | |
| DE | 8620898 U1 | | 2/1987 | |
| EP | 726743 | | 8/1996 | |
| GB | 1328551 | | 8/1973 | |
| JP | S6440065 A | | 2/1989 | |
| JP | 3036761 | | 2/1997 | |
| JP | 2001198145 A | | 7/2001 | |
| JP | 2003325556 A | | 11/2003 | |
| WO | WO 9400076 A1 | * | 1/1994 | ......... A61C 17/0202 |
| WO | 9408533 A1 | | 4/1994 | |
| WO | WO 2004034923 A1 | * | 4/2004 | ........... A61C 1/0092 |

* cited by examiner

DROPLET JET SYSTEM FOR CLEANSING

CROSS REFERENCE TO RELATED APPLICATION

This application claims the benefit of U.S. provisional application Ser. No. 60/537,690 filed 20 Jan. 2004, which is incorporated herein by reference.

This invention relates generally to cleaning systems using a fluid (liquid) stream, useful for cleaning teeth but also for other applications, and more specifically concerns such a cleaning system using a stream of fluid droplets.

Liquid jet cleaning devices/systems, typically involving a pulsed stream of water, are well known and are commercially available from several manufacturers. Such devices are used for various cleaning applications, including specifically oral care applications. Such oral care devices are useful primarily, however, for massaging of the gums and refreshment of the mouth as well as removal of food particles from between the teeth. Such devices, however, are ineffective in cleaning dental plaque from teeth, particularly hard-to-reach areas such as the gingival areas or the interproximal regions between the teeth.

In order to produce any significant cleaning having clinical benefit, including removal of dental plaque, i.e. biofilms, from teeth surfaces, fluid pressure of such a magnitude is required that significant discomfort to the user and damage to the gums result. Hence, such devices are not used for cleaning (plaque removal) of teeth or in other applications where the required fluid pressure may otherwise cause damage to the article being cleaned or its surroundings. Another disadvantage of such existing oral care devices/systems is the large amount of liquid (usually water) used, which typically is not comfortable in the mouth, i.e. the oral cavity, of a user.

In some cases, the stream of fluid is atomized into droplet form. This is shown and described in U.S. Pat. No. 5,820,373. However, the arrangement described in that patent, in particular the characteristics of the droplet, is designed to produce a disinfection of the periodontal pocket. The system is not useful for plaque removal. Droplets produced via an atomization process are also used in industrial cleaning applications. Such an application is shown in U.S. Pat. No. 6,332,470, U.S. Pat. No. 4,906,187 and EPO 726743, which all disclose a droplet spray system using air to atomize and accelerate droplets of water, with or without additives. However, those patents do not teach a droplet arrangement which is effective in oral cleaning, particularly removal of dental plaque, without causing discomfort and/or damage to the tissues of the oral cavity.

It is thus desirable to have a fluid system which provides effective oral cleaning (plaque-removing) results, particularly for hard-to-reach surfaces, without causing discomfort and/or damage to the user.

A system and corresponding method for cleaning teeth, comprising: a source of fluid; a fluid droplet generator for creating a stream of individual fluid droplets from the fluid, wherein the velocity of the droplets is within a range of 20 meters per second to 250 meters per second; and a member for directing the stream of droplets for cleaning selected oral surface one wherein the stream of droplets is otherwise characterized by a capability of removing biofilms from the oral surface area without discomfort or damage to the teeth or surrounding tissues of the user.

The present invention also includes a fluid droplet system for cleaning teeth, comprising: a source of fluid; and a fluid droplet generator and directing assembly for creating a stream of individual fluid droplets from the fluid and directing them for cleaning a selected oral care surface area, wherein effective fluid droplets have a diameter greater than 5 microns and have a velocity greater than 20 meters per second, and wherein the effective fluid droplets have a combined specific momentum of approximately at least $3 \times 10^3$ Newton·meters$^{-2}$ to produce a sufficient cleaning effect to remove biofilm from the oral surface area without discomfort to damage to the teeth or surrounding tissues of the user.

The present invention is directed toward a cleaning system using a succession (spray) of fluid droplets, wherein cleaning is particularly effective for the oral cavity, removing biofilm, i.e. dental plaque, from the teeth, including from hard-to-reach areas, such as below the gum line, or interproximally, without discomfort to the user or damage to the tissues in the oral cavity. The droplets have selected characteristics and the system itself has particular operating parameters relative to the droplets to produce the advantageous results of effective cleaning (including plaque removal) without discomfort and/or damage. In the present invention, the small size of the droplets produces effective cleaning of the very small crevices in the teeth, where stains caused by food residue and bacteria tend to accumulate. Effective stain removal is another advantageous result of the present invention.

These characteristics and operating parameters include, in particular, the velocity of the droplets, the size of the droplets and the frequency of the droplets, i.e. the number of droplet impacts upon a selected surface area in a selected period of time. Other characteristics/parameters include the angle of impact, the viscosity of the fluid and the surface tension of the fluid, among others. There may be other important characteristics presently unknown.

The droplet spray of the present invention distributes energy over a relatively large area, allowing a small number of high energy droplets to be applied to a given small spot in the larger area. If the same amount of liquid were applied in the form of a focused jet of drops, one immediately behind the other, the energy in the droplets would be concentrated in a smaller area, i.e. a spot or a line. If too much energy is applied to a given spot, damage is caused. By breaking (dispersing) the liquid into many small droplets, it is possible to apply the totality of energy over a relatively large area, such that the high energy in the droplets is sufficient to remove dental plaque, but not high enough to cause damage. Like a chisel, enough energy must be applied to a given spot to produce results, but with only the necessary number of hits to avoid undesired damage.

Figure 1:
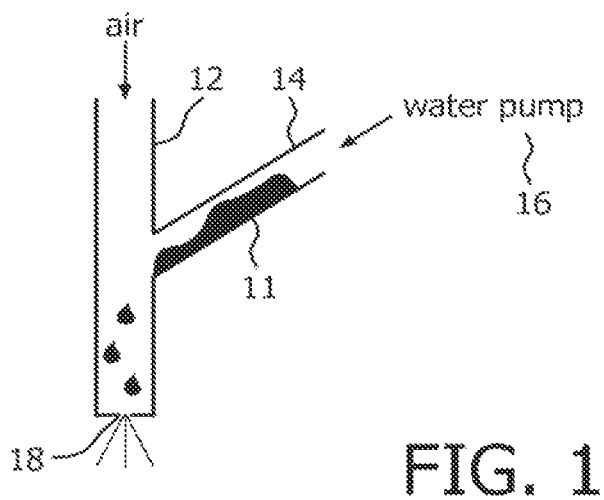
FIG. 1 shows a simplified diagram showing one embodiment for creating fluid droplets in a cleaning system of the present invention using a high speed stream of air.

In general, the present system involves the creation of fluid droplets, dispersed in the form of a spray or wide stream, and the acceleration of the droplets to the desired velocity. One embodiment of the present invention is shown in FIG. 1. In FIG. 1, a fluid 11 is introduced to a fast flowing stream of air moving through a tube 12. Fluid 11 is introduced to tube 12 through inlet member 14. Fluid 11, such as for instance water, is moved through inlet 14 by a pump 16; alternatively the tube 12 can be physically narrowed in front of where water inlet tube 14 joins tube 12, which results in a lower pressure region in air tube 12, which in turn draws fluid 11 into the air tube.

Such an arrangement, involving the addition of fluid in flowing stream of air, has been shown to be effective in removing dental plaque from teeth in vivo.

In operation the liquid (water) 11 breaks up into droplets when it comes into contact with the fast moving air stream. The droplets are then accelerated by the continuing air stream until typically they reach nearly the same velocity as the flowing air, and are then directed outwardly from tube 12 through nozzle 18. In one example, the flowing air is under 2 bar pressure, although this could be somewhat less, i.e. 1 bar, or greater, 3 bar or even more. Tube 12 in the particular embodiment shown is 3 mm in diameter, with a round nozzle approximately 0.7 mm in diameter and 1.5 mm long. A piston type pump 16 is used in one embodiment to pump fluid at a rate of 60 ml per minute; alternatively, the rate could be 30 ml or less, providing a maximum of 60 ml of fluid over a two minute period. The above nozzle results in a spray 2 mm wide at a distance of 3 mm from the nozzle. Other size nozzles could be used. For instance a 0.4 mm nozzle has been used successfully.

As indicated above, velocity of the droplets is an important characteristic. A suitable range of velocity is typically 20 meters per second to 250 or 300 meters per second, depending on droplet size (diameter) with a preferred range in one embodiment of 70-100 m/s for 10 micron droplets and 20-60 m/s for 100 micron droplets. In another embodiment, the velocity is just greater than 20 m/s. Droplet size is an important characteristic, also as indicated above. Typically, the droplets will be greater than 5 microns, preferably larger (in some embodiments) than 10 microns, up to approximately 200 microns. In one embodiment, a preferred range is 10-30 microns. In another embodiment, a preferred range is 5-100 microns. The flow rate of the fluid into the mouth may also be significant relative to comfort of the user. Typically, in one embodiment, the flow rate will not exceed more than 20 ml per cleaning event, as this is the approximate amount of fluid which can be accommodated comfortably in the mouth during a given cleaning event. However, flow rates could be up to 100 ml per cleaning or could be somewhat larger than 20 ml, e.g. 40 ml. In another embodiment, the total amount of fluid in the mouth during a single brushing event will be approximately 60 ml or less.

Still further, the frequency or rate of droplet impact could be in the range of $10^4$-$10^9$ droplets per second. Typically, with such an arrangement, effective cleaning is produced at a distance of at least up to 3 mm (possibly up to 10 mm) between the teeth and the tip (end) of the nozzle.

The dispersion of the fluid into droplets is significant to ensure the desired area of impact. For instance, in one embodiment for dental plaque removal, the area of coverage should be at least 1 mm$^2$ but not more that 1 cm. Smaller areas may result in user discomfort, while larger areas will produce less effective results.

In general, for the arrangement of FIG. 1, cleaning will increase with the air pressure, which accelerates the various droplets. The flow of fluid can also be optimized for cleaning by modifying the nozzle configuration.

Figure 2:
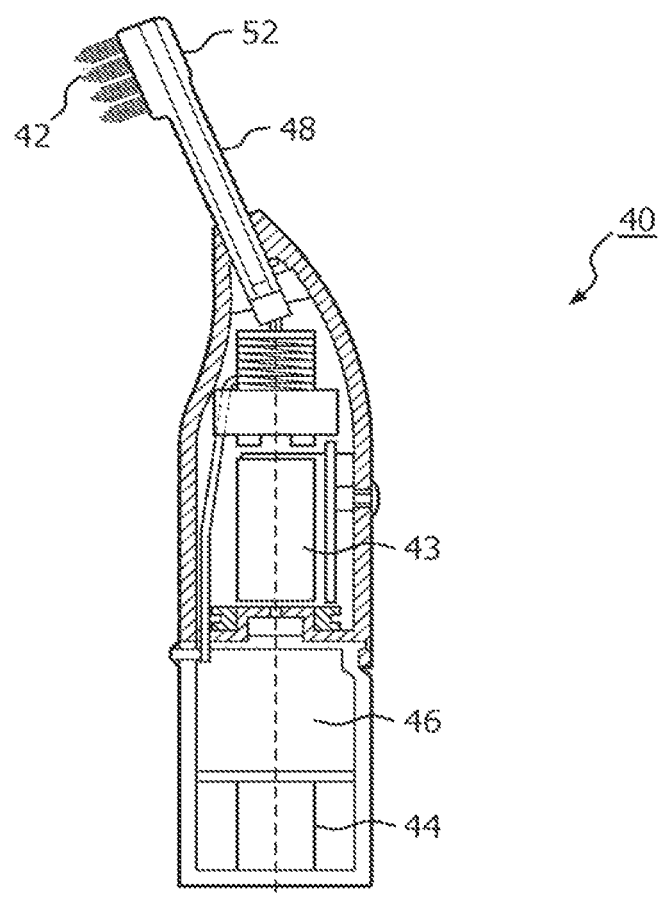
FIG. 2 is an elevational view showing another embodiment of the present invention using a plural nozzle arrangement, with fluid being forced through the nozzles under pressure.

The embodiment of FIG. 1 is directed toward the use of a gas (air) at high velocities, accelerating fluid which is added to the air stream. FIG. 2 shows another embodiment of the fluid droplet cleaning system of the present invention. This embodiment is shown specifically in the form of a toothbrush, generally at 40. In the embodiment shown, a plurality of small nozzles 42 (only one is shown for simplicity of illustration) produce droplets as fluid is forced through them under pressure. A fluid reservoir for the toothbrush is shown at 43, and is approximately 10 cm long. A spring 44 drives a piston 46, which in the embodiment shown has a face area of 2 cm$^2$. The spring is arranged so as to provide a pressure in the general range of 30-70 bar, even up to 100 bar. Fluid from the reservoir 43 is directed to a hollow stem portion 48 in the neck of the toothbrush and out through the plurality of nozzles 42 in brushhead 52.

In the embodiment shown, there are 10 separate nozzles in the brushhead, with each nozzle having a diameter in the range of 10-50 microns, preferably approximately 26 microns. There could be fewer nozzles, however, (or more); even one nozzle could work. The nozzles are approximately 200 microns long. The nozzles 42 are integrated into the brushhead and are made of flexible material, such as rubber, to prevent clogging. The fluid exiting from the nozzles breaks up into a spray of droplets at short distances from the nozzle itself. With appropriate pressure (see above), a nozzle size of 26 microns and a nozzle length of 200 microns, the droplets exit from the nozzle at 30 meters per second (or in another embodiment, at least 20 meters per second), at a rate (frequency) of 2.5 MHz (total for all 10 nozzles). The volume of water (with 10 nozzles) is approximately 10 ml/minute, in this embodiment. This arrangement provides effective cleaning without causing pain or discomfort to the user. Typically, without perturbation, the fluid will break up into droplets a short distance from the nozzle.

Figure 3:
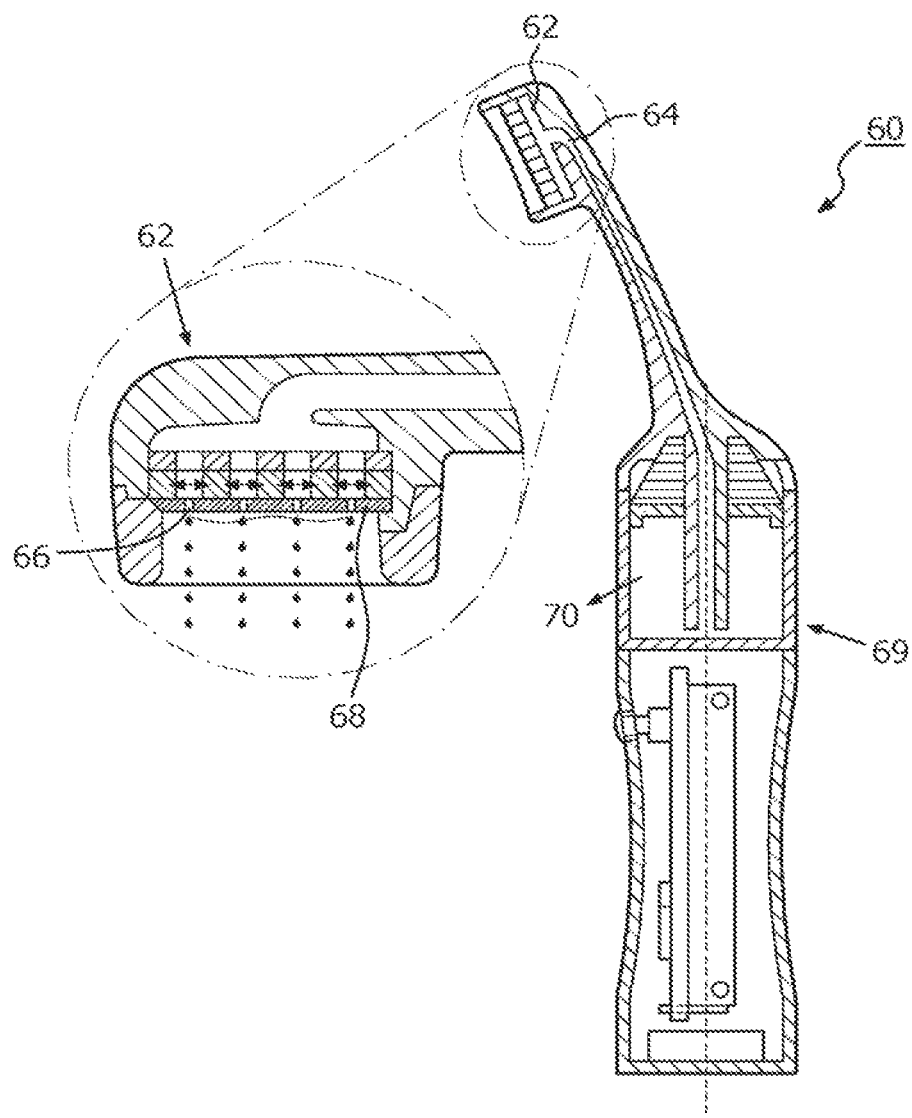
FIG. 3 is another embodiment of the present invention using a piezoelectric droplet-generating system.

Another embodiment is shown in FIG. 3, also in the form of a toothbrush, shown generally at 60. In this embodiment, a piezoelectric transducer element 62 (one frequency example is 1.5 MHz, but other frequencies are possible) is positioned in a head portion 64 of the toothbrush. The action of the piezoelectric element produces a high-speed pumping effect on the fluid, accelerating the fluid significantly through a set of nozzles 66 positioned in front of the piezoelectric element. There could be only one nozzle, in a particular embodiment.

As the fluid moves through the small nozzles 66, in nozzle plate 68, it breaks up into consistent-size small droplets.

Toothbrush 60 includes in a handle portion 69 a reservoir for fluid 70, the reservoir 70 being under a small but sufficient pressure to move the fluid from reservoir 70 to the droplet head. The action of the piezoelectric element accelerates the fluid through the nozzles 66. As the fluid is forced through the nozzles 66, it breaks up into drops within the range of 50-700 microns, typically depending on the size of the nozzles. In another embodiment, for instance, with a different size nozzle, the lower end of droplet diameter could be 5 microns.

The reservoir 70 for the fluid in one embodiment has a capacity of approximately 20 ml, which is the average amount used by a user for a mouthwash or cleaning event, typically two-minutes. In other embodiments, the capacity could be greater, for instance, 60 ml in one specific embodiment. As indicated above, reservoir 70 is under pressure to force fluid through the nozzles 66. The velocity and other characteristics of the droplets are substantially the same as for the other embodiments. The generation of the droplets, however, is different from the other embodiments. Reservoir 70 is under pressure, as for the embodiment of FIG. 2, delivering the fluid to the piezoelectric element.

It should be understood that other embodiments are possible for creating the droplets, besides those described specifically herein and variations thereof. For instance, inkjet techniques (conventional as well as future) can be used, where droplets are pushed out of capillary-type elements by contraction of surrounding piezoelectric elements. Further, fluid can be moved into contact with an ultrasound sonotrode, which breaks up the fluid into a mist.

As indicated above, various aspects of the droplet system have an effect on cleaning, notably velocity of the droplets, size of the droplets, and overall water flow i.e. fluid flux, among others.

Figure 4:
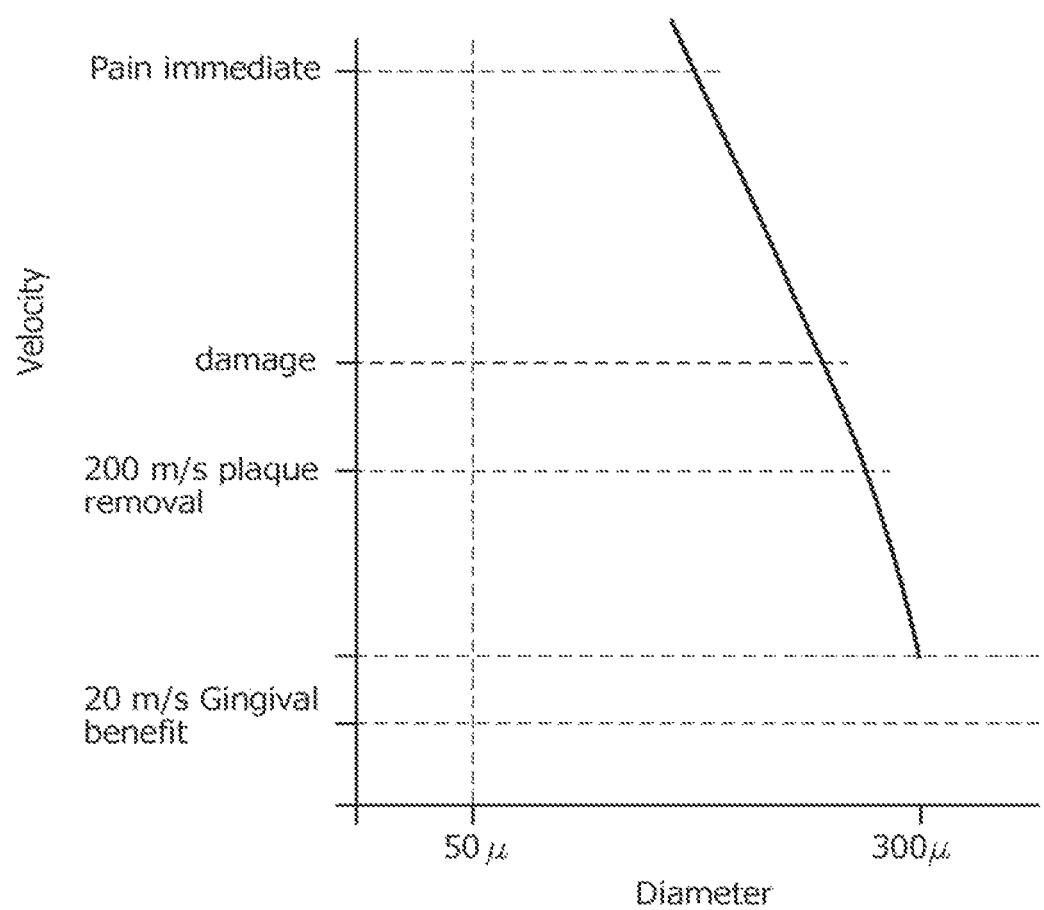
FIG. 4 is a graph showing droplet velocity on one axis v droplet size (diameter) on the other axis.

FIG. 4 is a diagram which shows the effect of the system operation, velocity v droplet size, with velocity ranging from 20 to 200 meters per second (and higher) and droplet size ranging from 5 microns to 300 microns. At low velocities, a gingival massage effect will occur, over a relatively wide range of droplet size. At low velocities, loose bacteria, bacterial products and loose food particles are removed from the teeth areas, including gingival pockets and interproximal areas. As the velocity increases, the cleaning effect in the mouth increases, including dental plaque removal and stain removal, up through damage and then significant discomfort to the user. Droplet size also has an effect on cleaning, although not as significant as velocity. Again, as indicated above, other factors, including angle, distance, flow rate and overall droplet rate (frequency) may also have a significant effect on cleaning.

The fluid used in the droplet system arrangement can vary, including water or water in combination with various chemical solutions, including various mouthwash solutions, antimicrobial solutions, fluoride, desensitizing agents, whitening solutions and other fluids, e.g. other beneficial oral care compounds or chemistries. Gas bubbles/solid particles can also be included in the fluid droplets. The system can be used successfully for cleaning hard-to reach oral areas, as well as orthodontia and dental implants. Still further, while the system has been disclosed specifically in the context of a toothbrush, where it results in the removal of dental plaque, particularly in hard to reach areas, without discomfort to the user, a result not previously accomplished by known water jet or droplet arrangements, the present invention can also be used for other cleaning applications. These include various surfaces in home care, dishwashing, laundry and stain removal. In these arrangements, active cleaning compounds or abrasives can be added to the water for different cleaning effects.

The "specific momentum" (defined below) of "effective" fluid droplets within a spray of droplets ("effective" fluid droplets being defined as droplets greater than 5 microns in diameter and moving with a velocity greater than 20 meters per second) has been discovered to be a significant factor relative to cleaning of the teeth, including interdental and subgingival cleaning, without causing discomfort or damage to the teeth or surrounding tissues of the mouth of the user. "Effective" fluid droplets are a subset of all of the fluid droplets in the spray, the effective fluid droplets producing the safe, effective cleaning. "Specific momentum" is defined herein as the time-averaged sum of the momenta of all the effective fluid droplets per unit surface area for a unit of time, for a spray which contacts an oral (tooth or teeth) surface, without the spray moving with respect to the oral surface, expressed in Newton·meters$^{-2}$. The area of the spray in contact with the oral surface is defined as the total, time-averaged, landing (impact) area of the spray. The above special definitions should be understood to be generalized for the case of pulsed mode operation of a fluid droplet system.

The different fluid possibilities are discussed above. Further, the range of droplet diameter in the present system is also discussed above, as well as ranges of droplet velocity.

Generally, however, when "specific momentum" is considered, it is preferred that the "effective" fluid droplets be greater than 5 micrometers in diameter and that the velocity of such droplets be at least 20 m/s, preferably at least 30 m/s. The diameter and velocity of the effective droplets individually may vary, as long as the sum of the momenta (per unit area per unit time) of all the effective fluid droplets is equal to or greater than the specific momentum necessary for safe and effective cleaning. Generally, for a droplet fluid such as water or similar fluids, including various mouthwashes, the combined specific momentum of all effective fluid droplets will be greater than 10 Newton·meters$^{-2}$ to at least $3 \times 10^5$ Newton·meters$^{-2}$, and perhaps greater, before damage/discomfort begins to occur. More preferably, the range is 100 Newton·meters$^{-2}$ to at least $3 \times 10^4$ Newton·meters$^{-2}$, with a most preferred threshold (minimum) value of $3 \times 10^3$ Newton·meters$^{-2}$. These ranges of momentum, for the set of said effective fluid droplets within a fluid droplet spray, will provide effective cleaning, including interdental and gum line (subgingival) cleaning without discomfort or damage to the teeth/gums of the user.

The importance of the "specific momentum" of "effective" fluid droplets indicates the interdependence of individual, and the entire set of, effective droplet sizes (volumes) and velocities relative to oral cleaning.

The effective fluid droplet specific momentum ranges and thresholds discussed above, furthermore, are effective for both low pressure and high pressure droplet systems, as well as gas-assisted (and non-gas-assisted) systems. A gas-assisted system is described in a co-pending application owned by the assignee of the present invention.

The effective fluid droplet specific momentum threshold indicated above produces effective and safe cleaning with a total fluid droplet spray volume in the mouth during a cleansing event, typically of 2 minutes, of less than 60 ml. As indicated above, the droplets may be produced by various means, including a pump or piezo-electric generator, in combination with nozzles of various configurations, as discussed above.

Hence, a cleaning system has been disclosed which is particularly effective as a complete and comprehensive oral care apparatus and method, combining cleaning of dental plaque with massaging of the gums and overall refreshment of the oral cavity.

Although preferred embodiments have been disclosed for purposes of illustration, it should be understood that various changes, modifications and substitutions may be made in such embodiments without departing from the spirit of the invention, which is defined by the claims which follow.

The invention claimed is:

1. A liquid droplet system for cleaning teeth, comprising:
a toothbrush head having a plurality of nozzles configured within the head, wherein each of the plurality of nozzles has an unobstructed exit end;
a source of air;
a source of liquid; and
a liquid droplet generator and directing assembly configured to create a stream of individual liquid droplets by accelerating liquid from the source of liquid with an air stream from the source of air and direct the individual liquid droplets in the form of a spray for cleaning a selected oral surface area, wherein the individual liquid droplets include a subset of effective liquid droplets that each have a diameter greater than 5 microns and a velocity greater than 20 meters per second, and wherein the subset of effective liquid droplets has a combined specific momentum within the range of $3\times10^3$ Newton meters$^{-2}$ to $3\times10^4$ Newton meters$^{-2}$, effective to remove biofilm from the oral surface area without discomfort or damage to the teeth or surrounding tissues of the user, and wherein the liquid droplet generator and directing assembly includes the toothbrush head having the plurality of nozzles.

2. The system of claim 1, wherein the said cleaning effect occurs with a volume of the liquid in the mouth of no more than 60 milliliters for a single cleaning event.

3. A system of claim 2, wherein the volume is within the range of 20-60 milliliters.

* * * * *